United States Patent
Gygax et al.

(10) Patent No.: US 9,763,979 B2
(45) Date of Patent: Sep. 19, 2017

(54) CARDIOPLEGIC PREPARATION

(75) Inventors: Erich Gygax, Bern (CH); Thierry Carrel, Bern (CH); Hendrik Tevaearai, Bern (CH)

(73) Assignee: Universitat Bern, Bern (CH)

( * ) Notice: Subject to any disclaimer, the term of this patent is extended or adjusted under 35 U.S.C. 154(b) by 468 days.

(21) Appl. No.: 13/059,517

(22) PCT Filed: Aug. 10, 2009

(86) PCT No.: PCT/IB2009/053505
§ 371 (c)(1),
(2), (4) Date: Mar. 21, 2011

(87) PCT Pub. No.: WO2010/020904
PCT Pub. Date: Feb. 25, 2010

(65) Prior Publication Data
US 2011/0183010 A1    Jul. 28, 2011

(30) Foreign Application Priority Data

Aug. 22, 2008 (WO) ................. PCT/IB2008/053377

(51) Int. Cl.
*A61P 9/00* (2006.01)
*A61K 33/14* (2006.01)
*A61P 41/00* (2006.01)
*A61K 33/06* (2006.01)
*A61K 33/00* (2006.01)
*A61K 9/00* (2006.01)
*A61K 9/08* (2006.01)
*A61K 31/245* (2006.01)
*A61K 31/7004* (2006.01)
*A61K 45/06* (2006.01)

(52) U.S. Cl.
CPC ............ *A61K 33/00* (2013.01); *A61K 9/0019* (2013.01); *A61K 9/08* (2013.01); *A61K 31/245* (2013.01); *A61K 31/7004* (2013.01); *A61K 33/06* (2013.01); *A61K 45/06* (2013.01)

(58) Field of Classification Search
CPC ...... A61K 33/00; A61K 33/06; A61K 31/245; A61K 31/7004; A61K 45/06; A61K 9/08; A61K 9/0019

USPC .................................................. 424/679, 682
See application file for complete search history.

(56) References Cited

FOREIGN PATENT DOCUMENTS

| WO | WO 86/00812 | * | 2/1986 | |
| WO | 2007/105179 | | 9/2007 | |
| WO | WO2007/105179 | * | 9/2007 | ........... A61K 31/245 |

OTHER PUBLICATIONS

Shakerinia et al. (Summary: Can. J. Surg. 1996, 39(5): 397-400) which is obtained via http://www.ncbi.nlm.nih.gov/pubmed/8857989.*
Albert et al. (Asian Cardiovascular & Thoracic Annals, 2004, 12, 2, 115-120).*
Shiroishi, M. S. (Texas Heart Institute Journal, 1999, 26, 1, 71-86).*
Hölscher (Arzneim.-Forsch. Drug Res. (1981) vol. 31(11) pp. 1881-1884).*
Sellevold et al. (Anesth. Analg. 1995;81:932-938).*
Holscher, B. (Arzneim-Forsch/Drug. Res. 1981, 31 (II), No. 11, 1881-1884).*
International Search Report for PCT/IB2009/053505, mailed Jun. 4, 2010.
Written Opinion of the International Searching Authority for PCT/IB2009/053505, mailed Jun. 4, 2010.
Jynge "Protection of the Ischemic Myocardium: Cold Chemical Cardioplegia, Coronary Infusates and the Importance of Cellular Calcium Control", Thoracic and Cardiovascular Surgeon, Thieme Med. Pub., New York, NY, US, vol. 28, No. 5, Jan. 1, 1980, pp. 310-321, XP008081445.
Mayne Pharma (NZ) Limited: "Procaine Hydrochloride Injection" [online], Oct. 4, 2006, pp. 1-8, XP002581186, Product Data Sheet Retrieved form the Internet: URL:http://www.medsafe.govt.nz/profs/datasheet/p/ProcaineHClinj.htm> p. 4.
Rudolf Voigt: "Lehrbuch Dr Pharmazeutischen Technologie", Jan. 1, 1984, VEB Verlag Volk und Gesundheit Berlin, Berlin, pp. 539-540, XP002581187.

* cited by examiner

Primary Examiner — Mina Haghighatian
Assistant Examiner — Helen Chui
(74) Attorney, Agent, or Firm — Nixon & Vanderhye P.C.

(57) ABSTRACT

The present invention relates to a cardioplegic preparation. According to a preferred embodiment of the invention, the preparation is made of two solutions, the first containing magnesium sulfate, potassium and xylitol, and the other containing procaine.

2 Claims, No Drawings

CARDIOPLEGIC PREPARATION

This application is the U.S. national phase of International Application No. PCT/IB2009/053505, filed 10 Aug. 2009, which designated the U.S. and claims priority to International Application No. PCT/IB2008/053377, filed 22 Aug. 2008, the entire contents of each of which are hereby incorporated by reference.

FIELD OF THE INVENTION

The invention relates to cardiac surgery. It more precisely concerns a cardioplegic preparation which can be used during cardiac surgery.

STATE OF THE ART

Various techniques have been used in clinical settings to arrest and protect the heart, and subsequently allowing operation on and in the heart. Although potassium and cold are considered standard approaches to achieve this goal, several implementations have been proposed over the last decades. Interestingly however, no single approach has been unanimously accepted by the community of cardiac surgeons and although cardiac surgery is today considered as much safer than a couple decades ago, all cardioplegia techniques have shown disadvantages. In fact, even though cardioplegic strategies are used to protect the myocardium during open heart procedures, one can still considers that the cardiac tissue is still suffering from ischemic as well as reperfusion injuries.

DESCRIPTION OF THE INVENTION

The invention relates to a cardioplegic preparation containing at least magnesium and potassium.

Advantageously the preparation is initially made of two separate solutions, the first containing said magnesium component and the second containing a local anesthetics, e.g. procaine.

In a preferred embodiment the two solutions are containing the following components:
Solution A: Magnesium
  Potassium
  Xylitol
Solution B: Procaine The solutions are buffered so that the pH after mixture of both solutions is between 5.5 and 7.0

Advantageously the following molecules are used:
Solution A: Magnesium sulfate heptahydrate
  Potassium chloride
  Xylitol
Solution B: Procaine hydrochloride Variations can include the following added component:
Adenosine Variations can also use:
Instead of Procaine, xylocain and/or Novocain and/or any other local anesthetics compatible with the components used in the preparation
Instead of Xylitol, Manitol and/or any sugar compatible with the other components used in the preparation
Magnesium chloride instead of Magnesium sulfate For one dose, the following ranges of quantities are advantageously used:

| Solution A: | Magnesium sulfate heptahydrate | 3-5 g |
| | Potassium chloride | 0.1-1.0 g |
| | Xylitol | 1-10 g |
| Solution B: | Procaine hydrochloride | 0.1-1.0 g |

Water is used to have a final volume (solution A+solution B) of 20 to 250 ml.

Solution A is buffered with citric acid monohydrate to a pH of 5.5 to 7.0.

The following preparation is preferably used:

| Solution A: | Magnesium sulfate heptahydrate | 4 g | 16.2 mmol |
| | Potassium chloride | 0.746 g | 10.0 mmol |
| | Xylitol | 4.5 g | 29.6 mmol |
| | Citric acid monohydrate | 1.061 g | 5.0 mmol |
| | Water for injection to a final volume of 95 ml | | |
| Solution B: | Procaine hydrochloride | 0.3 g | 1.1 mmol |
| | Water for injection to a final volume of 5 ml | | | pH of the mixed ready to use solution is 6.0.

The preparation is hyperosmolar with an osmolarity of the mixed ready to use solution of approximately 850 mosmol/l.

Pharmacological Tests

Several pharmacologic tests have been performed and lead to the preparation according to the invention. After several unsuccessful attempts it became possible to obtain a preparation that is stable and sterile over several months. In addition, the preparation according to the invention offers the advantage of avoiding the known incompatibility between procaine and sulfate Importantly, the tests have also demonstrated that at 2-8° C. and within the first 60 minutes following the mixing of solutions A and B, this incompatibility is not relevant.

As compared to previous cardioplegic solutions the preparation according to the invention has a higher potassium concentration. Experimental and clinical tests have both confirmed a reduced bioavailability of Potassium ions when in presence of xylitol and/or citric acid. By increasing thus the initial content of potassium in the cardioplegic solution, the concentration necessary to achieve the cardioplegic effect is guaranteed. In addition, clinical tests have confirmed that no potassium overdose is achieved.

As compared to previous cardioplegic solutions pH is also reduced to 6.0 which interestingly and advantageously allows to increase the effect of procaine.

Production

Solution A is prepared in a sterile way and stored in a vial with 95 ml. Solution B is also prepared in a sterile way and separately stored in a light protected 5 ml syringe.

Surgical Environment

At least 3-4 hours before the surgical procedure, the solutions are stored at 2-8° C. The ready to use solution (100 ml) is obtained by injecting the content of the syringe (solution B, 5 ml) into the vial (solution A, 95 ml). This resulting mixture is administered within 60 minutes after mixing, preferably within 15 minutes after mixing.

Clinical Tests

The preparation according to the invention was tested in several patients. The combination of the compounds was even tested in more than 3,000 patients and showed clear advantages as compared to traditional cardioplegic solutions. Not only the administration is simplified, but the cardiac arrest is almost instantaneous allowing thus the surgeon to immediately focus on his surgical procedure. Indeed, in most other cardioplegic strategies, the surgeon has to deliver a much larger quantity of solution and wait up to 5 minutes until the heart is considered ready to be operated on. Additionally, the current solution allows arrest and protection usually for more than 45-60 minutes whereas other solutions traditionally need to be repeated every 20 minutes. Clinical results are significantly superior since several of the post-operative complications can be reduced such as the rate of post-operative cardiac arythmias. More importantly, the preparation according to the invention can be integrated in the concept of new extra corporeal circulation (ECC) machines which aim to reduce or eliminate the trauma of such devices. This was recently confirmed in one study which showed in particular a significant reduction of post-ECC inflammatory reactions. A significant reduction of post-operative level of cardiac enzymes was observed. This confirms a better myocardial protection.

Advantages Provided by the Invention

As compared to other state of the art cardioplegic solutions, the cardioplegic preparation according to the invention presents several significant advantages, in particular:
1. The presentation with two separated solutions allows to prevent the consequences of the known incompatibility between sulfate and procain.
2. Mixing the two solutions at 2 to 8° C. allows to prevent abnormal formation of microparticles within at least one hour.
3. Production can be performed at room temperature before sterilization. Both solutions can then be considered stable for more than 9 months at room temperature. This can be considered a significant advantage since production can be amplified and products can be stocked and the entire logistics is facilitated.
4. Immediate injection of the freshly mixed preparation in the coronary arteries allows immediate cardiac arrest.
5. Because the solution is concentrated in a low volume (only 100 ml), hemodilution is prevented.
6. Cardioplegic effect is prolonged and usually maintained for of at least 60 minutes.
7. Administration is simplified since the preparation can be directly and rapidly injected into the aorta by the surgeon himself.
8. The preparation is particularly adapted for coronary artery bypass operations. Several studies have been performed in hospitals. They included thousands of patients. They all confirmed that a significantly better myocardial protection can be achieved. Indeed, the experience shows that the level of post-operative cardiac enzymes, in other words markers of cardiac cellular lesions, is reduced as compared to other cardioplegic solutions.

The invention claimed is:
1. A dose of a cardioplegic preparation consisting essentially of:
   a solution A consisting essentially of:
      magnesium sulfate heptahydrate 3-5 g
      potassium chloride 0.1-1.0 g
      xylitol 1-10 g
      water to a final volume of solution A that is 95% of a final volume of said dose, and
   a solution B consisting essentially of:
      procaine hydrochloride 0.1-1.0 g
      water to a final volume of solution B that is 5% of the final volume of said dose, wherein the final volume of said dose is 100 ml, and wherein solution A is buffered with citric acid monohydrate to a pH of 5.5 to 7.0.
2. A dose of a cardioplegic preparation consisting essentially of:
   a solution A consisting essentially of:
      magnesium sulfate heptahydrate 4 g
      potassium chloride 0.746 g
      xylitol 4.5 g
      citric acid monohydrate 1.061 g
      and water to a final volume of solution A that is 95 ml of a final volume of said dose,
   and
   a solution B consisting essentially of:
      procaine hydrochloride 0.3 g
      and water to a final volume of solution B that is 5 ml of the final volume of said dose.

* * * * *